(12) United States Patent
Chan et al.

(10) Patent No.: US 6,207,084 B1
(45) Date of Patent: Mar. 27, 2001

(54) NAPHTHOPYRANS ANNELATED IN C6-C7, THEIR PREPARATION AND COMPOSITIONS AND (CO)POLYMER MATRICES CONTAINING THEM

(75) Inventors: You-Ping Chan; Patrick Jean, both of Lyons (FR)

(73) Assignee: Corning S.A., Avon Cedex (FR)

( * ) Notice: Subject to any disclaimer, the term of this patent is extended or adjusted under 35 U.S.C. 154(b) by 0 days.

(21) Appl. No.: 09/393,953

(22) Filed: Sep. 9, 1999

(30) Foreign Application Priority Data

Sep. 11, 1998 (FR) .................................................. 98 11518

(51) Int. Cl.⁷ ............................. G02B 5/23; C07D 93/04; C07D 471/00; C07D 335/04
(52) U.S. Cl. ........................... 252/586; 524/110; 524/90; 546/47; 549/23; 549/382
(58) Field of Search ............................ 252/586; 524/110, 524/90; 549/382, 23; 546/47

(56) References Cited

U.S. PATENT DOCUMENTS

| 5,451,344 | 9/1995 | Knowles et al. |
| 5,645,767 | 7/1997 | Van Gemert |
| 5,651,923 | 7/1997 | Kumar et al. |
| 5,783,116 | 7/1998 | Lin |
| 5,891,368 | 4/1999 | Kumar |
| 6,018,059 * | 1/2000 | Chan ................................. 549/382 |
| 6,022,495 * | 2/2000 | Kumar ............................... 252/586 |

FOREIGN PATENT DOCUMENTS

| WO 95/27914 | 10/1995 | (WO) . |
| WO 98/28289 | 7/1998 | (WO) . |
| WO 99/23071 | 5/1999 | (WO) . |

* cited by examiner

Primary Examiner—Deborah C. Lambkin
(74) Attorney, Agent, or Firm—Angela N. Nwaneri; Peter Rogalskyj

(57) ABSTRACT

The present invention relates to novel naphthopyrans having a cyclic group annelated in position 6,7. These naphthopyrans have formula (I) given below:

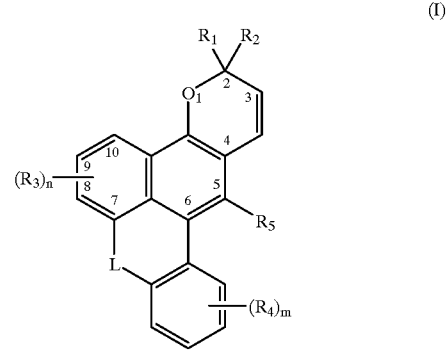

These compounds (I) have advantageous photochromic properties. The invention also covers a method of preparing these naphthopyrans, as well as their applications as photochromes and compositions and (co)polymers matrices comprising them.

26 Claims, No Drawings

NAPHTHOPYRANS ANNELATED IN C6-C7, THEIR PREPARATION AND COMPOSITIONS AND (CO)POLYMER MATRICES CONTAINING THEM

The present invention relates to novel naphthopyran-type compounds which have, in particular, photochromic properties. The invention also relates to photochromic compositions and photochromic ophthalmic articles (lenses for example) which contain said naphthopyrans. The invention also covers the preparation of these novel naphthopyrans.

The photochromic compounds are capable of changing colour under the influence of a poly- or mono-chromatic light (UV for example) and of returning to their initial colour when the luminous irradiation ceases, or under the influence of temperature and/or a poly- or mono-chromatic light different from the first.

The photochromic compounds find applications in various fields, e. g. for the manufacture of ophthalmic lenses, contact lenses, solar protection glasses, filters, camera optics or photographic apparatus optics or other optical devices and observation devices, glazing, decorative objects, bill elements or even for information storage by optical inscription (coding).

In the field of ophthalmic optics, and in particular the spectacles trade, a photochromic lens which comprises one or more photochromic compounds must have:

a high transmission in the absence of ultraviolets, a low transmission (high colourability) under solar irradiation, adapted coloration and discoloration kinetics, a tint acceptable to the consumer (grey or brown preferably) with preferably a maintenance of the chosen tint during the coloration and the discoloration of the lens, a maintenance of the performances, the properties, within a temperature range of 0–40° C., a significant durability, since these objectives sought after are sophisticated corrective lenses and therefore expensive.

These lens characteristics are in fact determined by the active photochromic compounds which they contain; compounds which must furthermore be perfectly compatible with the organic or inorganic support which constitutes the lens.

Moreover, it is to be noted that obtaining a grey or brown tint may necessitate the use of at least two photochromes of different colours, i.e. having distinct maximal absorption wavelengths in the visible. This combination further imposes other requirements of the photochromic compounds. In particular, the coloration and discoloration kinetics of the (two or more) combined active photochromic compounds must be essentially identical. The same applies for their stability with time et also for their compatibility with a plastic or inorganic support.

Amongst the numerous photochromic compounds described in the prior art, benzopyrans or naphthopyrans may be cited which are described in patents or patent applications U.S. Pat. Nos. 3,567,605, 3,627,690, 4,826,977, 5,200,116, 5,238,981, 5,411,679, 5,429,744, 5,451,344, 5,458,814, 5,651,923, 5,645,767, 5,698,141, WO-A-95 05382, FR-A-2,718,447, WO-A-96 14596, WO-A-97 21698 which are of the reduced formula below:

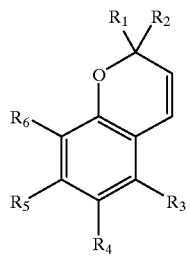

U.S. Pat. Nos. 5,645,767 and 5,651,923 more specifically describe naphthopyrans having, respectively, firstly indeno groups, and secondly benzo or naphthofurano groups on side f of the naphthopyran (general structures below).

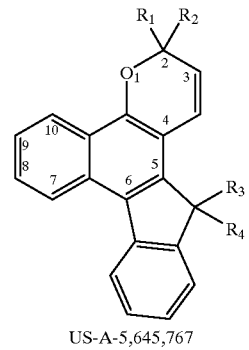

US-A-5,645,767

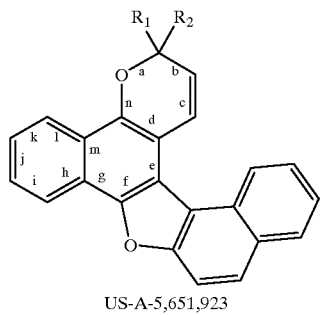

US-A-5,651,923

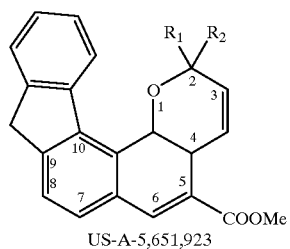

US-A-5,651,923

It appears that some of the naphthopyrans disclosed in U.S. Pat. No. 5,651,923 comprise indene-type annelated carbocycles which are fused with carbons 9 and 10 of the naphthopyran unit, or comprise benzo- or naphthofuran-type annelated heterocycles which are fused with carbons 5 and 6 of the naphthopyran unit.

The photochromic compounds according to U.S. Pat. No. 5,645,767 are obtained from substituted or non-substituted benzophenones which are allowed to react with a succinic acid ester such as the dimethyl ester, in the presence of toluene and potassium tert-butoxide. A half-ester is thus produced which is successively converted into acetoxynaphtalene and carboxynaphthol which are cyclised to give a naphthol fused with an indenone residue. The reaction of this latter compound with a propargylic alcohol, in the presence of DBSA leads to a naphthopyran fused with an indenone ring. The indene homologue of this naphthopyran can be obtained by starting off with the precursor having a reduced ketone function. This carbon of the indene can be substituted in various ways.

As for the naphthopyrans fused with benzo- or naphthofuran- residues according to U.S. Pat. No. 5,651,923, they are prepared by the reaction of a naphthol fused with an indenone ring or a naphthofuran ring, on the one hand, and with a propargylic alcohol on the other. The naphthol fused with an indenone ring is obtained for example as described in U.S. Pat. No. 5,645,767; while the naphthol fused with a naphthofuran ring originates from the reaction between a naphthoquinone and a 1,3-dihydroxynaphthalene, with or without subsequent methylation of at least one hydroxy.

These compounds claim to satisfy the specifications defined above. In reality, if these compounds really do have one or more of the basic properties sought after, such as a high transmission in the absence of ultraviolets and a high colourability under solar irradiation, none of the compounds described hitherto have the complete combination of the properties sought after which are necessary for the production of satisfactory articles. In particular, none of these compounds is intrinsically grey or brown and the necessity of using an additional photochrome in order to obtain one of these two tints does subsist.

In this context, it is to the credit of the inventors for having been interested in this type of naphthopyran as a base for developing novel photochromes, and for having proposed a novel family of molecules which have particularly advantageous photochromic properties.

Thus, according to a first of its aspects, the present invention relates to naphthopyran compounds of the following formula (I):

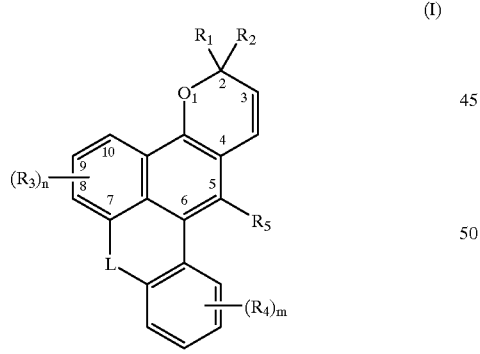

(I)

in which:

L corresponds to a direct bond or to a divalent residue: O, S, $NR_6$, ($R_6$ represents a linear or branched alkyl group which comprises 1 to 6 carbon atoms), $CR_7R_8$, $(CR_7R_8)_2$, $R_7C=CR_8$ ($R_7$ and $R_8$, which are identical or different, independently representing an H, an OH, a linear or branched alkyl or alkoxy group which comprises 1 to 6 carbon atoms) or a carbocycle selected from the following:

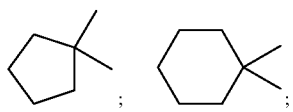

$R_1$ and $R_2$ independently represent:
  a hydrogen,
  a linear or branched alkyl group which comprises 1 to 12 carbon atoms,
  a cycloalkyl group which comprises 3 to 12 carbon atoms,
  an aryl or heteroaryl group which comprises in its basic structure 6 to 24 carbon atoms or 4 to 24 carbon atoms respectively and at least one heteroatom selected from sulphur, oxygen and nitrogen; said basic structure being optionally substituted with at least one substituent selected from:
    a halogen, and notably fluorine, chlorine and bromine,
    a hydroxy group,
    a linear or branched alkyl group comprising 1 to 12 carbon atoms,
    a linear or branched alkoxy group comprising 1 to 12 carbon atoms,
    a haloalkyl or haloalkoxy group corresponding to the ($C_1$–$C_{12}$) alkyl or alkoxy groups above respectively which are substituted with at least one halogen atom, and notably a fluoroalkyl group of this type,
    a linear or branched alkenyl group comprising 2 to 12 carbon atoms, and notably a vinyl group or an allyl group,
    an —$NH_2$ group,
    an —NHR group, R representing a linear or branched alkyl group comprising 1 to 6 carbon atoms,
    a

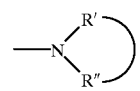

group, R' and R", which are identical or different, independently representing a linear or branched alkyl group comprising 1 to 6 carbon atoms, or representing together with the nitrogen atom to which they are bound a 5- or 7-membered ring which can comprise at least one other heteroatom selected from oxygen, sulphur and nitrogen, said nitrogen being optionally substituted with an R'" group, which is a linear or branched alkyl group comprising 1 to 6 carbon atoms,
    a methacryloyl group or an acryloyl group,
  an aralkyl or heteroaralkyl group, the alkyl group, which is linear or branched, comprising 1 to 4 carbon atoms and the aryl and heteroaryl groups having the definitions given above, or
  said two substituents $R_1$ and $R_2$ together form an adamantyl, norbornyl, fluorenylidene, di($C_1$–$C_6$) alkylanthracenylidene or spiro($C_5$–$C_6$) cycloalkylanthracenylidene group; said group being optionally substituted with at least one of the substituents listed above for $R_1$, $R_2$: an aryl or heteroaryl group;
$R_3$ and $R_4$, which are identical or different, independently represent:

a hydrogen,
a halogen, and notably fluorine, chlorine or bromine,
a linear or branched alkyl group which comprises 1 to 12 carbon atoms (advantageously 1 to 6 carbon atoms),
a cycloalkyl group comprising 3 to 12 carbon atoms,
a linear or branched alkoxy group comprising 1 to 12 carbon atoms (advantageously 1 to 6 carbon atoms),
a haloalkyl, halocycloalkyl, or haloalkoxy group corresponding to the alkyl, cycloalkyl, alkoxy groups above respectively, which are substituted with at least one halogen atom, notably selected from fluorine, chlorine and bromine,
an aryl or heteroaryl group having the same definition as that given supra for $R_1$, $R_2$,
an aralkyl or heteroaralkyl group, the alkyl group, which is linear or branched, comprising 1 to 4 carbon atoms, and the aryl and heteroaryl groups having the same definitions as those given supra for $R_1$, $R_2$,
an amine or amide group: —$NH_2$, —NHR, —$CONH_2$, —CONHR,

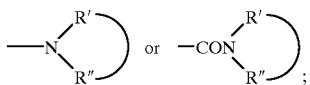

R, R', R" having their respective definitions given supra for the amine substituents of the values $R_1$, $R_2$: aryl or heteroaryl,
an —$OCOR_6$ or —$COOR_6$ group, $R_6$ representing a straight or branched alkyl group comprising 1 to 6 carbon atoms, or a cycloalkyl group comprising 3 to 6 carbon atoms, or a phenyl group, optionally substituted with at least one of the substituents listed above for the values of $R_1$, $R_2$: aryl or heteroaryl;
m and n are, independently, integers of 0 to 4 and of 0 to 3 respectively;
$R_5$ represents:
a hydrogen,
a linear or branched alkyl group which comprises 1 to 12 carbon atoms (advantageously 1 to 6 carbon atoms),
a cycloalkyl group which comprises 3 to 12 carbon atoms,
a linear or branched alkenyl group which comprises 2 to 12 carbon atoms, and notably a vinyl group or an allyl group,
a phenyl or benzyl group, optionally substituted with at least one of the substituents listed above for the values of $R_1$, $R_2$: aryl or heteroaryl,
a group —$COR_7$, —$COOR_7$ or $CONHR_7$, $R_7$ representing a linear or branched alkyl group comprising 1 to 6 carbon atoms, or a cycloalkyl group comprising 3 to 6 carbon atoms, or a phenyl or benzyl group optionally substituted with at least one of the substituents listed above in the definition of the radicals $R_1$, $R_2$ in formula (I), in the case in which these radicals correspond independently to an aryl or heteroaryl group.

The compounds of the invention—naphthopyrans of formula (I)—possess particularly advantageous photochromic properties. More specifically, these novel compounds have a high colourability, (even at 40° C.), a high sensitivity to UV with higher λmax's than the known naphthopyrans of analogous structure.

Amongst said compounds of formula (I) above, preferred are those which have the formula (I 1) below:

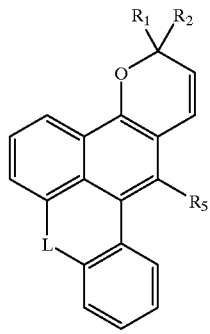

in which:
L represents a direct bond, an oxygen, a radical —$CH_2$—

or the carbocycle below:

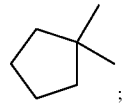

$R_1$ and/or $R_2$, independently represent optionally substituted aryl or heteroaryl groups the basic structure of which is selected from those of phenyl, naphthyl, biphenyl, pyridyl, furyl, benzofuryl, dibenzofuryl, N—($C_1$–$C_6$)alkylcarbazole, thienyl, benzothienyl, dibenzothienyl, julolidinyl groups; $R_1$ and/or $R_2$ advantageously representing a para-substituted phenyl group or $R_1$ and $R_2$ together form an adamantyl or norbornyl group;

$R_5$ represents a hydrogen, a linear or branched alkyl group which comprises 1 to 6 carbon atoms, an optionally substituted phenyl or benzyl group, a —$COR_7$, —$COOR_7$, or $CONHR_7$ group, $R_7$ representing a linear or branched alkyl group comprising 1 to 6 carbon atoms, or an optionally substituted phenyl or benzyl group.

Amongst the above compounds of formula (I) and (II) are particularly prefered those which are different from the ones having L corresponding to a direct bond and $R_5$ being $COOR_7$ or $CONHR_7$ (sub-family I' or I 1') and more generally those of said formulae (I) and (II) in which L (does not correspond a direct bond) corresponds to a divalent residue: O,S, $NR_6$, $CR_7R_8(CR_7R_8)_2$, $R_7C$=$R_8$ or to a carbocycle (sub-family I" or I1").

The inventors also take the credit in that they have proposed, in this field of photochromes, a novel synthetic route to annelated naphthopyrans which gives access to novel compounds which possess at least one carbocycle or heterocycle fused with carbons 6 and 7 of the naphthopyran unit, this synthetic route making use of a naphthol-type precursor which is obtained from at least one ketone:
which comprises at least one carbocycle or heterocycle;
and which is allowed to react with at least one alkyl cyanoacetate;

the product obtained being then subjected to a cyclisation.

According to a second of its aspects, the invention also relates to a method of preparation, notably a method of preparation of the compounds of formula (I) as defined supra.

This method essentially consists in carrying out a condensation:

of at least one compound of formula (II) below:

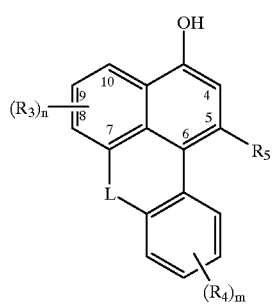

(II)

in which $R_3$, $R_4$, $R_5$, L, m and n are as defined above with reference to formula (I);

with at least one derivative of propargylic alcohol, of formula (III) below:

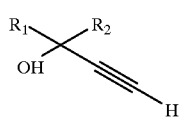

(III)

in which $R_1$ and $R_2$ are as defined above with reference to formula (I);

the condensation (II)/(III) being advantageously carried out in the presence of a catalyst, this catalyst being preferably selected from the group comprising: para-toluenesulphonic acid, dodecylsulphonic acid and bromoacetic acid, or with an aldehyde derivative, of formula (III') below:

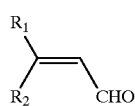

(III')

in which $R_1$ and $R_2$ are as defined above with reference to formula (I);

the condensation (II)/(III') being advantageously carried out in the presence of a metallic complex, preferably a complex of titanium, titanium (IV) ethoxide being particularly preferred.

In practice, the condensation reaction between compounds (II) and (III) can take place in solvents such as toluene, xylene or tetrahydrofuran, to which appropriate catalysts are optionally added.

For more details on the condensation of compounds (II'), (III'), reference may be made to the EP-A-0 562 915 patent application.

Said compounds of formula (III) are known to the person skilled in the art and are obtained from the corresponding ketone according to a method described notably in the WO-A-96 14596 patent application. The ketone is itself commercial or is prepared according to the known methods such as the Friedel Crafts method (cf. WO-A-96 14596 and cited references). Aldehydes derived from (III), are obtained by rearrangement in an acid medium (cf. *J. Org. Chem.,* 1977, 42, 3403).

Said compounds of formula (II) are obtained according to a synthetic scheme the various steps of which are adaptations of known methods. The preferred general synthetic scheme is given below:

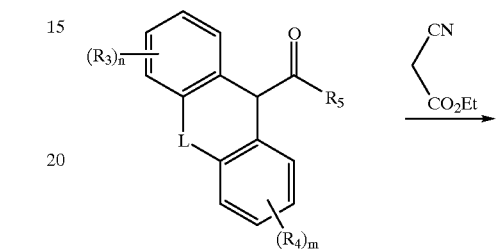

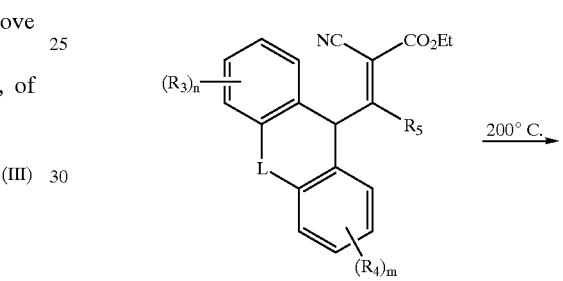

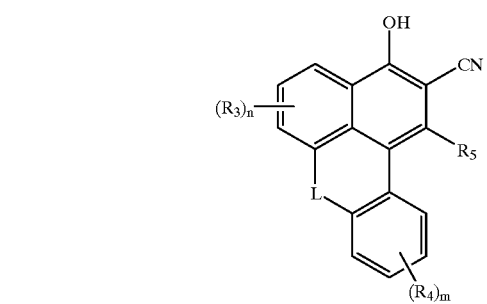

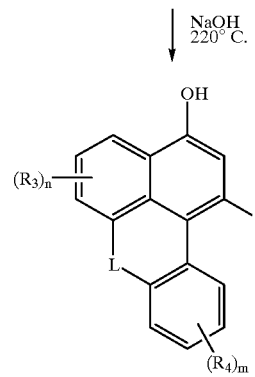

This synthetic route is inspired from the work of Sepiol et al. (*Synthesis* 1979, 290)

From where it ensues that the invention also covers a method of preparing the naphthols of formula (II), characterised in that it comprises the following essential steps:

1—Reaction of a precursor ($Ip_1$) of formula:

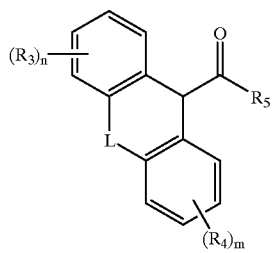

($Ip_1$)

with at least one alkyl cyanoacetate of formula NC—$CH_2$—$COOR^a$ with $R^a$=alkyl preferably ethyl, so as to obtain the intermediate product ($Ip_2$):

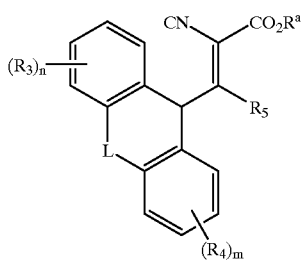

($Ip_2$)

2—Thermal cyclisation of ($Ip_2$) leading to the intermediate ($Ip_3$):

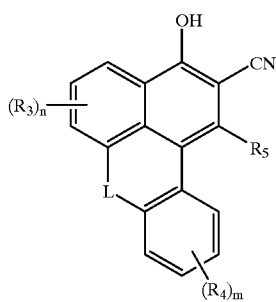

($Ip_3$)

3—High temperature decyanation of ($Ip_3$) to produce the intermediate (II):

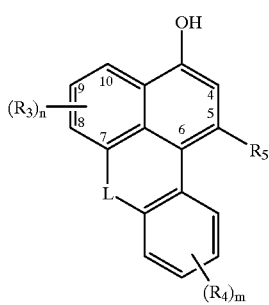

(II)

The details on the whole of this method are given in the following Examples. It really is a matter of a novel synthetic route in the field of photochromes; and this route offers undeniable advantages in terms of ease of implementation and in economical terms.

According to a third of its aspects, the object of the invention is a (co)polymer and/or a reticulate obtained by polymerising and/or cross-linking at least one monomer comprising a naphthopyran as defined supra. Thus, the naphthopyrans according to the invention can be per se (co)monomers and/or be comprised in (co)polymerisable and/or cross-linkable (co)monomers. The (co)polymers and/or reticulates thus obtained can constitute photochromic matrices.

According to a fourth of its aspects, the present invention relates to the use of said compounds of formula (I) of the invention as photochromic agents. The object of the invention is, therefore:

firstly, novel photochromic compounds which are constituted by the naphthopyran derivatives such as defined above, taken alone or in a mixture of themselves and/or with at least one other photochromic compound of another type and/or with at least one non-photochromic colouring agent;

secondly, novel photochromic compositions which comprise at least one naphthopyran derivative (I), and one of its derivatives as defined above, and/or at least one linear or cross-linked (co)polymer containing at least one compound (I) according to the invention in its structure. Such photochromic compositions can contain at least one other photochromic compound, of another type and/or at least one non-photochromic colouring agent and/or at least one stabilising agent. The photochromic compounds of another type, non-photochromic colouring agents, and stabilising agents are prior art products known to the person skilled in the art.

Within the context of the present invention, combinations of photochromic compounds of the invention and/or combinations of photochromic compounds of the invention and photochromic compounds of another type according to the prior art are particularly recommended; such combinations being interesting in that they are suitable for generating grey or brown tints, which are desired by the public in applications such as ophthalmic spectacles or solar spectacles. These additional photochromic compounds can be those known to the person skilled in the art and described in the literature, e. g. chromenes (U.S. Pat. Nos. 3,567,605, 5,238, 981, WO-A-94 22850, EP-A-0 562 915), spiropyrans or naphthospiropyrans (U.S. Pat. No. 5,238,981) and spiroxazines (Crano et al., "Applied Photochromic Polymer Systems", Ed. Blackie & Son Ltd, 1992, chapter 2).

Said compositions according to the invention can also comprise:

non-photochromic colouring agents which enable adjusting the tint, and/or one or more stabilising agents, such as an antioxidising agent for example, and/or one or more anti-UV, and/or one or more anti-radicals, and/or one or more photochimic excited state deactivators.

These additives can notably enable improving the durability of said compositions.

The compounds of the invention envisaged within the context of their photochromic applications can be used in solution. Thus, a photochromic solution can be obtained by dissolving at least one of said compounds in an organic solvent such as toluene, dichloromethane, tetrahydrofuran or ethanol. The solutions obtained are in general colourless and transparent. When exposed to sunlight, they develop a strong coloration and regain the colourless state when they are placed in an area of less exposure to the sun's rays or, in other words, when they are no longer submitted to UV. In general, a very low concentration of product (of the order of 0.01 to 5% by weight) is sufficient to obtain an intense coloration.

The compounds according to the invention are furthermore compatible with support matrices of organic polymer or of inorganic material, in a form included in said matrices as well as in the form of a coating of said matrices.

Also, within the context of the fourth aspect of the invention in relation to the photochromic applications, the object of the invention is a matrix which comprises:

at least one compound (I), as defined supra;

and/or at least one (co)polymer and/or reticulate, as defined supra;

and/or at least one composition, as presented above.

The most interesting applications of the compounds of the invention are in fact those in which the photochrome is dispersed uniformly within or on the surface of a matrix formed by a polymer, a copolymer and/or mixture of (co)polymers.

Following the example of their behaviour in solution or in a polymer matrix, the compounds according to the invention are colourless or slightly coloured in the initial state and rapidly develop an intense coloration under a UV light (365 nm) or under a light source of the solar type. Finally, they regain their initial coloration once the irradiation ceases.

The methods of implementation which can be envisaged in order to obtain such a matrix are very varied. Amongst those known to the person skilled in the art, the diffusion in the (co)polymer, from a suspension or solution of the photochrome, in a silicone oil, in an aliphatic or aromatic hydrocarbon, or in a glycol, or from another polymer matrix, can be cited for example. The diffusion is commonly carried out at a temperature of 50 to 200° C. for a period of time of 15 minutes to several hours, according to the nature of the polymer matrix. Another implementation technique consists in mixing the photochrome in a formulation of polymerisable matrices, depositing this mixture on a surface or in a mould, and then carrying out the copolymerisation. These implementation techniques, and others, are described in the article by Crano et al. "Spiroxazines and their use in photochromic lenses" published in Applied Photochromic Polymer Systems, Ed. Blackie and Son Ltd- 1992.

The following products may be mentioned as examples of preferred polymer materials for forming matrices which are useful in optical applications of the photochromic compounds according to the invention:

alkyl, cycloalkyl, (poly or oligo)ethylene glycol, aryl or arylalkyl mono-, di-, tri- or tetraacrylate or mono-, di-, tri- or tetramethacrylate, which is optionally halogenated or which comprises at least one ether and/or ester and/or carbonate and/or carbamate and/or thiocarbamate and/or urea and/or amide group, polystyrene, polyether, polyester, polycarbonate (e.g. bisphenol-A polycarbonate, diallyl diethylene glycol polycarbonate), polycarbamate, polyepoxy, polyurea, polyurethane, polythiourethane, polysiloxane, polyacrylonitrile, polyamide, aliphatic or aromatic polyester, vinylic polymers, cellulose acetate, cellulose triacetate, cellulose acetate-propionate or polyvinylbutyral, difunctional monomers having the formula below:

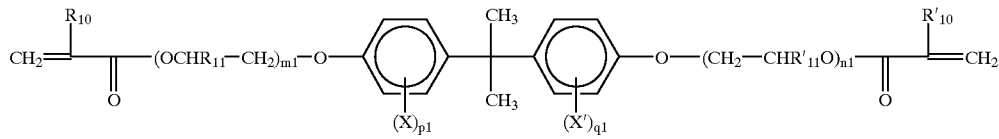

in which:

$R_{10}$, $R'_{10}$, $R_{11}$ and $R'_{11}$ are identical or different and represent independently a hydrogen or a methyl group;

$m_1$ and $n_1$ are, independently, integers between 0 and 4 (inclusive); and are advantageously independently equal to 1 or 2;

X and X', which are identical or different, are a halogen and represent, preferably, a chlorine and/or a bromine;

$p_1$ and $q_1$ are, independently, integers between 0 and 4 (inclusive);

copolymers of at least two types of copolymerisable monomers selected from the precursor monomers of the polymers listed supra, (notably those belonging to the group comprising: (meth)acrylic monomers, vinylic monomers, allylic monomers, and mixtures thereof).

In a particularly preferred manner, the photochromes of the invention are used with resins which have a nanobiphasic structure and which are obtained by copolymerising at leas two different, specific difunctional monomers. Such resins have been described in the French patent Application FR-A-2 762 845.

The amount of photochrome used in the (co)polymer matrix depends upon the degree of darkening desired. Usually, between 0.001 and 20% by weight of it is used.

Still according to the fourth of its aspects in relation to the applications of the naphthopyrans (I) as photochromes, another object of the present invention is ophthalmic articles, such as ophthalmic or solar spectacle articles, comprising:

at least one compound according to the invention, and/or at least one (co)polymer and/or reticulate formed, at least in part, from compound(s) of the invention, and/or at least one photochromic composition as defined above, and/or at least one matrix, as defined supra, of an organic polymer material or of an inorganic material, or even of a hybrid inorganic-organic material, said matrix initially optionally comprising at least one compound of the invention.

In practice, the articles which are more particularly covered by the present invention are ophthalmic lenses or photochromic solar lenses, glazing (windows for buildings, for locomotion engines, automobile vehicles), optical devices, decorative articles, solar protection articles, information storage, . . .

The present invention is illustrated by the Examples which follow of synthesis and of photochromic validation, of naphthopyrans of the invention. Said compounds of the invention are compared to a prior art compound, C1.

EXAMPLE 1

Synthesis of Compound (1)

Step 1

The following mixture: 10 g of 9-acetylfluorene (Brown et al., Tetrahedron Asymmetry 1996, 7, 2029), 5.47 g of ethyl cyanoacetate, 4 g of ammonium acetate, 2 g of acetic acid in 60 ml of toluene, is heated under reflux for 4 hours in a 100 ml conical flask equipped with a Dean-Stark collector. The reaction mixture is diluted with 50 ml of toluene and then washed with 200 ml of water and then 100 g of a saturated sodium bicarbonate solution. The solution is dried over magnesium sulphate and then evaporated to dryness. 15 g of a yellowish oil are obtained. A yield of 80% is estimated according to the proton NMR.

Step 2

The following mixture: 14 g of the product of the previous step in 15 g of acetamide is heated at 200° C. for 3 h. The mixture is then poured while hot into 300 ml of water under agitation. 2 extractions with dichloromethane (200+100 ml) are carried out. The organic phase is then washed with 2×100 ml of water, dried over magnesium sulphate and then reduced to dryness. A brown oil is obtained. The product is purified by chromatography on silica in eluting with toluene and then toluene/chloroform (1/1). The purest product-containing fractions are recovered and are reduced to dryness, 1.1 g (10%) of yellow powder are isolated.

Step 3

The following mixture: 1.0 g of the product of the previous step, 2 g of sodium hydroxide in 10 ml of ethanol, is heated at about 200–220° C. for 6 h in a 125 ml reactor (the pressure developed is about 30 bars). After cooling, the mixture is transferred into a flask and then reduced to dryness. The paste is then dissolved in 50 ml of water and then neutralised by the slow and progressive addition of concentrated hydrochloric acid. The precipitate is recovered by filtration, washed with 2×20 ml of water and then dried under vacuum at 40° C. overnight. Yield 0.9 g (99%).

Step 4

The following mixture: 0.6 g of the product of the previous step (2.58 mmole), 0.98 g of 1,1-bis(para-methoxyphenyl)propyn-1-ol (3.66 mmole), in the presence of a catalytic amount of bromoacetic acid in 10 ml of xylene, is heated under reflux for 3 hours in a 100 ml reactor. The mixture is then washed with 3×30 ml of 3N potassium hydroxide and then with 50 ml of water containing 2 g of NaCl. The product is then purified by a chromatography on silica in eluting with toluene. The purest fractions are combined and are reduced to dryness. After a recrystallisation from a toluene/diisopropyl ether mixture, 140 mg of compound (1) are recovered in the form of a clear yellow solid. Its structure is confirmed by NMR spectroscopy.

EXAMPLE 2

Synthesis of Compound (2)

Steps 1 to 3

The naphthol derivative is synthesised, in the same way as for the compound of Example 1, from methyl 9-xanthenyl ketone. (Rochlin et al., J. Amer. Chem. Soc., 1992, 114, 230).

Step 4

The following mixture: 1.0 g of the product of the previous step (4 mmole), 1.3 g of 1,1-bis(para-methoxyphenyl)propyn-1-ol (4.8 mmole) in the presence of a catalytic amount of bromoacetic acid in 15 ml of xylene, is heated under reflux for 2.5 hours. The mixture is then washed with 2×25 ml of 3N potassium hydroxide and then with 25 ml of water. The photochromic product is then isolated after 2 successive purifications by chromatography on a silica column (eluent heptane/toluene 70/30 and then ethyl acetate/heptane 20/80) followed by a recrystallisation from THF/ethanol. 150 mg of a clear yellow product are obtained. Yield 7.5%. Its structure is confirmed by proton NMR.

EXAMPLE 3

Synthesis of Compound (3)

The following mixture: 0.95 g of the naphthol from step 3 of the preceding synthesis (3.8 mmole), 1.25 g of 1-p-dimethylamino-phenyl-1-phenyl-propyn-1-ol (5.0 mmole) in the presence of a catalytic amount of bromoacetic acid in 15 ml of toluene, is heated under reflux for 1.5 h. The mixture is then diluted with 15 ml of THF and then neutralised with 1 g of sodium bicarbonate. The solution is then filtered and then reduced to dryness. The product is submitted to a purification by chromatography on a silica column in eluting with a toluene/heptane 70/30 mixture. The photochromic fractions are recovered, evaporated to dryness and then heated in a mixture of 5 ml of THF and 20 ml of heptane. After 2 hours of agitation at ambient temperature, the green-tinted crystallised product is recovered by filtration. Yield: 400 mg (32%). Its structure is confirmed by proton NMR.

EXAMPLE 4

Synthesis of Compound (4)

Step 1

9,9-spirocyclopentyl-10-acetyl-9,10-dihydroanthracene is prepared according to the following sequence: (1) Reduction of the spirocyclopentylanthrone (WO 96/30357) with sodium borohydride in trifluoroacetic acid (W. Gribble et al., Synthesis, 172, 1977); (2) Condensation of the organo-lithium reagent formed by the action of t-BuLi on acetaldehyde (W. Adam et al., Chem. Ber., (126), 2697, 1993), which leads to the alcohol; (3) Oxidation of the hydroxyl function to a carbonyl function with the aid of pyridinium chlorochromate (E. J. Corey et al., Tetrahedron Lett., 2647, 1975).

Step 2

The following mixture: 5.05 g of 9,9-spirocyclopentyl-10-acetyl-9,10-dihydroanthracene, 2.22 g of ethyl cyanoacetate, 1.1 ml of acetic acid, 6 g of ammonium acetate (1.5 g added every 4 hours) in 50 ml of toluene, is heated under reflux for 12 hours in a 100 ml conical flask equipped with a Dean-Stark collector.

5 g of acetamide are then added to the medium and the control temperature is increased to 250° C. After having distilled all the solvent off, the reflux of acetamide is kept up for 5 hours. The mixture is then poured, whilst hot, into 100 ml of water with stirring. 2 extractions with toluene/THF 1/1 (2×50 ml) are made. The organic phase is then washed with 30 ml of water and then 30 ml of a saturated sodium chloride solution, dried over magnesium sulphate and then reduced to dryness. A brown oil is obtained. The product is purified by chromatography on silica in eluting with a toluene/ diisopropyl ether mixture (1/1). The purest product-containing fractions are recovered which are reduced to dryness before recrystallising the desired product from toluene. 2.4 g (40%) of a yellow powder are isolated.

Step 3

The following mixture: 2.3 g of the product of the previous step, 2.6 g of sodium hydroxide in 30 ml of ethanol, is heated at about 200–220° C. for 5 h in a 125 ml reactor (the pressure developed is about 30 bars). After cooling, the mixture is transferred into a flask and then reduced to dryness. The paste is then dissolved in 100 ml of water and then neutralised by the slow and progressive addition of concentrated hydrochloric acid. The precipitate is recovered by filtration, washed with 2×20 ml of water and then dried under vacuum at 40° C. overnight. A brown solid is collected in quantitative yield.

Step 4

The following mixture: 750 mg of the product of the previous step, 670 mg of 1,1-bis(para-methoxyphenyl) propyn-1-ol, in the presence of a catalytic amount of bromoacetic acid in 20 ml of xylene, is heated under reflux for 4 hours in a 50 ml reactor. After evaporation of the solvent, the product is purified directly, firstly by a chromatography on silica gel in eluting with toluene, and then by a filtration on alumina gel. The purest fractions are combined and are reduced to dryness. 79 mg of compound (4) are recovered in the form of a violet oil. Its structure is confirmed by NMR spectroscopy.

EXAMPLE 5

Compound C1

Compound C1 of the prior art, of formula:

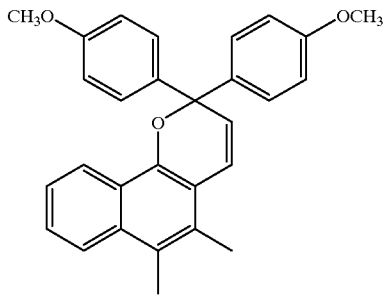

was considered.

This compound is commercially available.

EXAMPLE 6

The photochromic properties of said compounds (1) to (4) and C1 were evaluated.

Said compounds are dissolved, at the rate of 5 mg in 50 ml of THF. The UV-visible absorptions (optical path of 1 cm) are then measured before and after exposure to a 365 nm UV source. The observation of the tints and intensities developed is made by placing the solutions in the sun or before a solar simulator. The properties of these compounds are given in the Table below.

| Compound | Structure | λ1* | λ2** | T½ (discoloration) | Tint/ colourability |
|---|---|---|---|---|---|
| (1) | 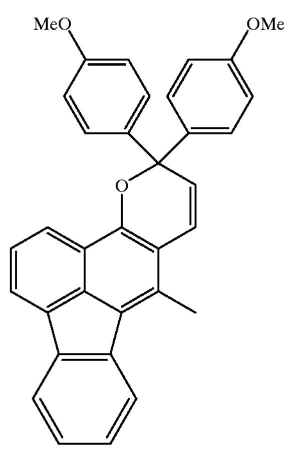 | 415 nm | 512 nm | 13 s | red/high |

-continued
| Compound | Structure | λ1* | λ2** | T½ (discoloration) | Tint/ colourability |
|---|---|---|---|---|---|
| (2) | 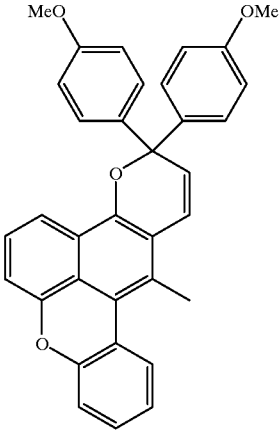 | 405 nm | 564 nm | 21 s | violet/high |
| (3) | 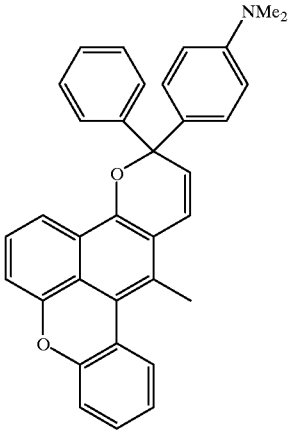 | 405 nm | 594 nm | 22 s | blue/high |
| (4) | 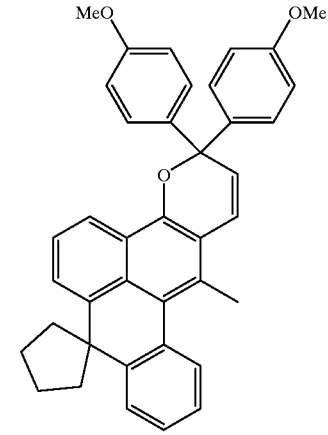 | 409 nm | 517 nm | 98 s | pink/high |

| Compound | Structure | λ1* | λ2** | T½ (discoloration) | Tint/ colourability |
|---|---|---|---|---|---|
| Cl | 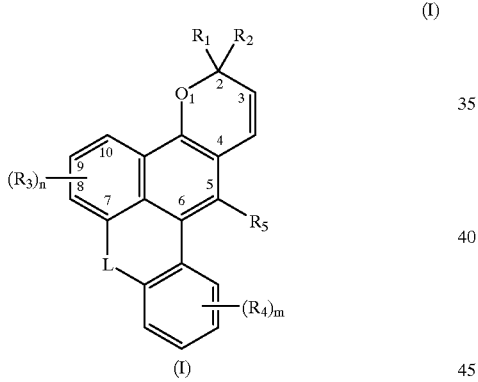 | 368 nm | 490 nm | 39 s | red/medium |

*λ max of the band of the longest wavelength of the compound before exposure.
**λ max of the band of the longest wavelength of the compound after exposure.

It is demonstrated by these measurements that the naphthopyrans of the invention have higher λ1's than the analogous compound without the ring annelated in position 6,7 of the naphthopyran, and this improves its sensitivity to solar radiation. The λ2's of the compounds are also higher (bathochromic shift) and the intensities developed in the presence of UV rays or solar rays are much higher than for the analogous compound.

What is claimed is:

1. Naphthopyrans of the following formula (I):

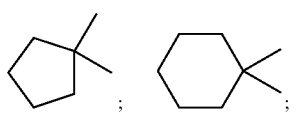

in which:

L corresponds to a direct bond or to a divalent residue selected from the group consisting of O; S; $NR_6$, where $R_6$ represents a linear or branched alkyl group which comprises 1 to 6 carbon atoms; $CR_7R_8$; $(CR_7R_8)_2$; $R_7C=CR_8$, where $R_7$ and $R_8$ are identical or different and independently represent a H, an OH group, or a linear or branched alkyl or alkoxy group which comprises 1 to 6 carbon atoms; and a carbocycle selected from the following:

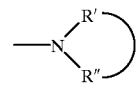

$R_1$ and $R_2$ independently represent:
a hydrogen,
a linear or branched alkyl group which comprises 1 to 12 carbon atoms,
a cycloalkyl group which comprises 3 to 12 carbon atoms,
an aryl group which comprises in its basic structure 6 to 24 carbon atoms or a heteroaryl group which comprises in its basic structure 4 to 24 carbon atoms and at least one heteroatom selected from sulphur, oxygen and nitrogen; said basic structure being optionally substituted with at least one substituent selected from:
a halogen,
a hydroxy group,
a linear or branched alkyl group comprising 1 to 12 carbon atoms,
a linear or branched alkoxy group comprising 1 to 12 carbon atoms,
a haloalkyl or haloalkoxy group corresponding to the ($C_1$–$C_{12}$) alkyl or alkoxy groups above respectively which are substituted with at least one halogen atom,
a linear or branched alkenyl group comprising 2 to 12 carbon atoms,
an —$NH_2$ group,
an —NHR group, R representing a linear or branched alkyl group comprising 1 to 6 carbon atoms,
a $$-N\diagdown_{R''}^{R'}$$

group, where R' and R" are identical or different and independently represent a linear or branched alkyl group comprising 1 to 6 carbon atoms, or represent together with the nitrogen atom to which they are bound a 5- or 7-membered ring which can comprise at least one other heteroatom selected from oxygen, sulphur, and nitrogen, said nitrogen being optionally substituted with an R'" group, which is a linear or branched alkyl group comprising 1 to 6 carbon atoms, and
a methacryloyl group or an acryloyl group,
an aralkyl or heteroaralkyl group, the alkyl group, which is linear or branched, comprising 1 to 4 carbon atoms and the aryl and heteroaryl groups having the definitions given above, or
said two substituents $R_1$ and $R_2$ together form an adamantyl, norbornyl, fluorenylidene, di($C_1$–$C_6$)

alkylanthracenylidene or spiro(C₅–C₆)cyclo-
alkylanthracenylidene group; said group being
optionally substituted with at least one of the sub-
stituents listed above for $R_1$, $R_2$: an aryl or heteroaryl
group;

$R_3$ and $R_4$, which are identical or different, independently
represent:
  a hydrogen,
  a halogen,
  a linear or branched alkyl group which comprises 1 to
    12 carbon atoms,
  a cycloalkyl group comprising 3 to 12 carbon atoms,
  a linear or branched alkoxy group comprising 1 to 12
    carbon atoms,
  a haloalkyl, halocycloalkyl, or haloalkoxy group cor-
    responding to the alkyl, cycloalkyl, alkoxy groups
    above respectively, which are substituted with at
    least one halogen atom,
  an aryl or heteroaryl group having the same definition
    as that given above for $R_1$, $R_2$,
  an aralkyl or heteroaralkyl group, the alkyl group,
    which is linear or branched, comprising 1 to 4 carbon
    atoms, and the aryl and heteroaryl groups having the
    same definitions as those given above for $R_1$, $R_2$,
  an amine or amide group: —NH₂, —NHR, —CONH₂,
    —CONHR,

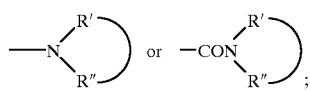

R, R', R'' having their respective definitions given
    above for the amine substituents of $R_1$, $R_2$: aryl or
    heteroaryl,
  an —OCOR₆ or —COOR₆ group, R₆ representing a
    straight or branched alkyl group comprising 1 to 6
    carbon atoms, or a cycloalkyl group comprising 3 to
    6 carbon atoms, or a phenyl group, optionally sub-
    stituted with at least one of the substituents listed
    above for the values of $R_1$, $R_2$: aryl or heteroaryl;

m and n are, independently, integers of 0 to 4 and of 0 to
  3 respectively;

$R_5$ represents:
  a hydrogen,
  a linear or branched alkyl group which comprises 1 to
    12 carbon atoms,
  a cycloalkyl group which comprises 3 to 12 carbon
    atoms,
  a linear or branched alkenyl group which comprises 2
    to 12 carbon atoms,
  a phenyl or benzyl group, optionally substituted with at
    least one of the substituents listed above for $R_1$, $R_2$:
    aryl or heteroaryl,
  a —COR₇, —COOR₇, or CONHR₇ group, R₇ repre-
    senting a linear or branched alkyl group comprising
    1 to 6 carbon atoms, or a cycloalkyl group compris-
    ing 3 to 6 carbon atoms, or a phenyl or benzyl group
    optionally substituted with at least one of the sub-
stituents listed above in the definition of the radicals
$R_1$, $R_2$ in formula (I), in the case in which these
radicals correspond independently to an aryl or het-
eroaryl group.

2. Naphthopyrans according to claim 1, of formula (I1):

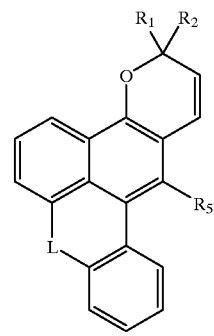

(I1)

in which:

L represents a direct bond, an oxygen, a radical

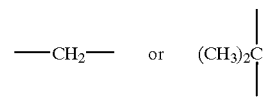

or the carbocycle:

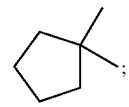

$R_1$ and $R_2$ independently represent optionally substituted
  aryl or heteroaryl groups the basic structure of which is
  selected from those of phenyl, naphthyl, biphenyl,
  pyridyl, furyl, benzofuryl, dibenzofuryl, N—(C₁–C₆)
  alkylcarbazole, thienyl, benzothienyl, dibenzothienyl,
  and julolidinyl groups; $R_1$ and $R_2$ represent a para-
  substituted phenyl group; or $R_1$ and $R_2$ together form
  an adamantyl or norbornyl group;

$R_5$ represents a hydrogen a linear or branched alkyl group
  which comprises 1 to 6 carbon atoms, an optionally
  substituted phenyl or benzyl group,
a —COR₇, —COOR₇, or —CONHR₇ group, R₇ repre-
  senting a linear or branched alkyl group comprising 1
  to 6 carbon atoms or an optionally substituted phenyl or
  benzyl group.

3. Naphthopyrans according to claim 1 in which L does
not correspond to a direct bond.

4. A method of preparing the naphthopyrans of formula (I)
according to claim 1, characterised in that it comprises
carrying out a condensation:

of at least one compound of formula (II) below:

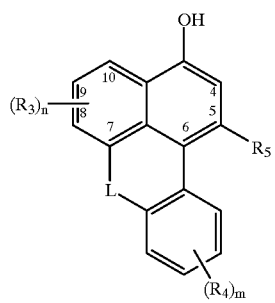

(II)

in which $R_3$, $R_4$, $R_5$, L, m, and n are as defined with reference to formula (I) in claim 1;

with a derivative of propargylic alcohol, of formula (III) below:

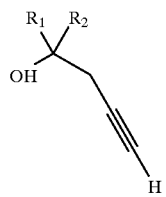

(III)

in which $R_1$ and $R_2$ are as defined with reference to formula (I) above;

the condensation (II)/(III) being optionally carried out in the presence of a catalyst selected from the group consisting of paratoluenesulphonic acid, dodecylsulphonic acid, and bromoacetic acid;

or with an aldehyde derivative, of formula (III') below:

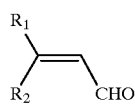

(III')

in which $R_1$ and $R_2$ are as defined with reference to formula (I) in claim 1;

the condensation (II)/(III') being optionally carried out in the presence of a metallic complex of titanium.

5. The method according to claim 4, characterised in that the starting compound (II) is produced by a method which comprises:

(a) reacting a precursor ($Ip_1$) of formula:

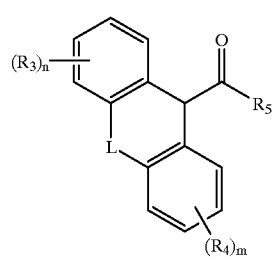

($Ip_1$)

with at least one alkyl cyanoacetate of formula $NC-CH_2-COOR^a$ with $R^a$=alkyl, so as to obtain the intermediate product ($Ip_2$):

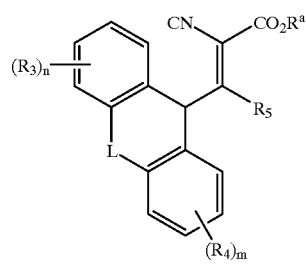

($Ip_2$)

(b) thermally cyclizing ($Ip_2$) to produce the intermediate ($Ip_3$):

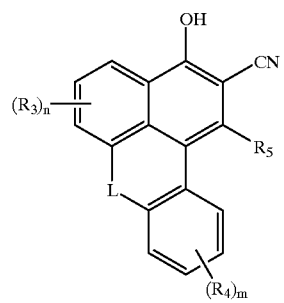

($Ip_3$)

and
(c) decyanating ($Ip_3$) at high temperatures to produce the intermediate (II):

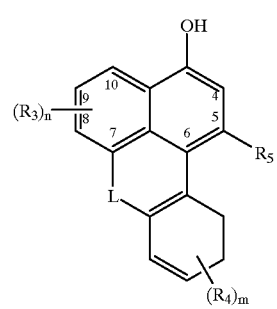

(II)

6. A (co)polymer and/or reticulate obtained by polymerising and/or cross-linking at least one monomer comprising at least one naphthopyran according to claim 1.

7. A photochromic compound, characterised in that it consists of a compound according to claim 1, or of a mixture of at least two compounds according to claim 1, or of a mixture of at least one compound according to claim 1 with at least one other photochromic compound of another type and/or at least one non-photochromic colouring agent.

8. A photochromic composition, characterised in that it comprises:

at least one compound according to claim 1, and/or at least one linear or cross-linked (co)polymer which contains, in its structure, at least one compound (I) according to claim 1; and optionally, at least one other photochromic compound of another type and/or at least one non-photochromic colouring agent and/or at least one stabilising agent.

9. A (co)polymer matrix, characterised in that it comprises:

at least one compound according to claim 1.

10. The matrix according to claim 9, characterised in that the (co)polymer is selected from the group consisting of:

an alkyl, cycloalkyl, (poly or oligo)ethylene glycol, aryl, or arylalkyl mono-, di-, tri- or tetraacrylate or mono-, di-, tri-, or tetramethacrylate, which is optionally halogenated or which comprises at least one ether and/or ester and/or carbonate and/or carbamate and/or thiocarbamate and/or urea and/or amide group, a polystyrene, polyether, polyester, polycarbonate, polycarbamate, polyepoxy, polyurea, polyurethane, polythiourethane, polysiloxane, polyacrylonitrile, polyamide, aliphatic or aromatic polyester, vinylic polymer, cellulose acetate, cellulose triacetate, cellulose acetate-propionate, or polyvinylbutyral, a difunctional monomer having the formula:

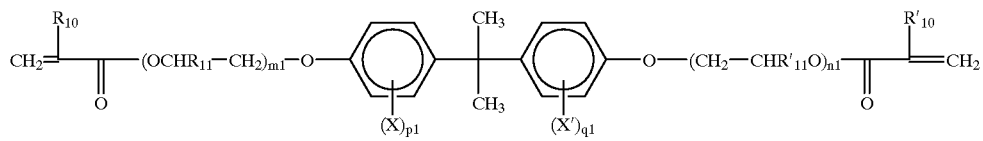

in which:

$R_{10}$, $R'_{10}$, $R_{11}$, and $R'_{11}$ are identical or different and represent independently a hydrogen or a methyl group;

$m_1$ and $n_1$ are, independently, integers between 0 and 4 inclusive;

X and X', which are identical or different, are halogens; and p1 and q1 are, independently, integers between 0 and 4 inclusive;

a copolymer of at least two types of copolymerisable monomers selected from the precursor monomers of the polymers listed above; and combinations thereof.

11. An ophthalmic or solar article comprising:

at least one compound according to claim 1.

12. The article according to claim 11, characterised in that it is constituted by a lens, by a glazing, or by an optical device.

13. A (co)polymer matrix, characterised in that it comprises:

at least one co(polymer) and/or reticulate according to claim 6.

14. The matrix according to claim 13, characterised in that the (co)polymer is selected from the group consisting of:

an alkyl, cycloalkyl, (poly or oligo)ethylene glycol, aryl, or arylalkyl mono-, di-, tri-, or tetraacrylate or mono-, di-, tri-, or tetramethacrylate, which is optionally halogenated or which comprises at least one ether and/or ester and/or carbonate and/or carbamate and/or thiocarbamate and/or urea and/or amide group, a polystyrene, polyether, polyester, polycarbonate, polycarbamate, polyepoxy, polyurea, polyurethane, polythiourethane, polysiloxane, polyacrylonitrile, polyamide, aliphatic or aromatic polyester, vinylic polymer, cellulose acetate, cellulose triacetate, cellulose acetate-propionate, or polyvinylbutyral, a difunctional monomer having the formula:

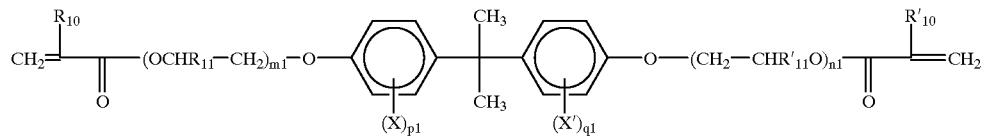

in which:

$R_{10}$, $R'_{10}$, $R_{11}$, and $R'_{11}$ are identical or different and represent independently a hydrogen or a methyl group;

$m_1$ and $n_1$ are, independently, integers between 0 and 4 inclusive;

X and X', which are identical or different, are halogens;

p1 and q1 are, independently, integers between 0 and 4 inclusive;

a copolymer of at least two types of copolymerisable monomers selected from the precursor monomers of the polymers listed above; and combinations thereof.

15. A (co)polymer matrix, characterised in that it comprises:

at least one composition according to claim 8.

16. The matrix according to claim 15, characterised in that the (co)polymer is selected from the group consisting of:

an alkyl, cycloalkyl, (poly or oligo)ethylene glycol, aryl, or arylalkyl mono-, di-, tri-, or tetraacrylate or mono-, di-, tri-, or tetramethacrylate, which is optionally halogenated or which comprises at least one ether and/or ester and/or carbonate and/or carbamate and/or thiocarbamate and/or urea and/or amide group, a polystyrene, polyether, polyester, polycarbonate, polycarbamate, polyepoxy, polyurea, polyurethane, polythiourethane, polysiloxane, polyacrylonitrile, polyamide, aliphatic or aromatic polyester, vinylic polymer, cellulose acetate, cellulose triacetate, cellulose acetate-propionate, or polyvinylbutyral, a difunctional monomer having the formula:

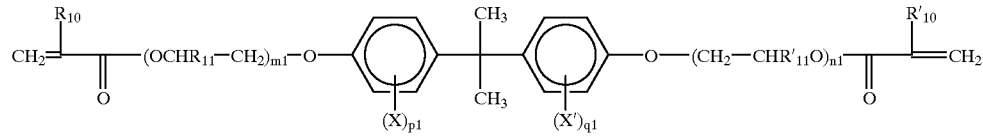

in which:
R$_{10}$, R'$_{10}$, R$_{11}$, and R'$_{11}$ are identical or different and represent independently a hydrogen or a methyl group;
m$_1$ and n$_1$ are, independently, integers between 0 and 4 inclusive;
X and X', which are identical or different, are halogens;
p1 and q1 are, independently, integers between 0 and 4 inclusive;
a copolymer of at least two types of copolymerisable monomers selected from the precursor monomers of the polymers listed above; and
combinations thereof.

17. An ophthalmic or solar article comprising:
at least one (co)polymer and/or reticulate according to claim 6.

18. The article according to claim 17, characterised in that it is constituted by a lens, by a glazing, or by an optical device.

19. An ophthalmic or solar article comprising:
at least one composition according to claim 8.

20. The article according to claim 19, characterised in that it is constituted by a lens, by a glazing, or by an optical device.

21. An ophthalmic or solar article comprising:
at least one matrix according to claim 9.

22. The article according to claim 21, characterised in that it is constituted by a lens, by a glazing, or by an optical device.

23. An ophthalmic or solar article comprising:
at least one matrix according to claim 13.

24. The article according to claim 23, characterised in that it is constituted by a lens, by a glazing, or by an optical device.

25. An ophthalmic or solar article comprising:
at least one matrix according to claim 15.

26. The article according to claim 25, characterised in that it is constituted by a lens, by a glazing, or by an optical device.

* * * * *